(12) United States Patent
Bhat

(10) Patent No.: US 10,440,246 B2
(45) Date of Patent: Oct. 8, 2019

(54) SYSTEM FOR ENABLING REMOTE ANNOTATION OF MEDIA DATA CAPTURED USING ENDOSCOPIC INSTRUMENTS AND THE CREATION OF TARGETED DIGITAL ADVERTISING IN A DOCUMENTATION ENVIRONMENT USING DIAGNOSIS AND PROCEDURE CODE ENTRIES

(71) Applicant: Kiran K. Bhat, Brooklyn, NY (US)

(72) Inventor: Kiran K. Bhat, Brooklyn, NY (US)

(*) Notice: Subject to any disclaimer, the term of this patent is extended or adjusted under 35 U.S.C. 154(b) by 508 days.

(21) Appl. No.: 15/157,129

(22) Filed: May 17, 2016

(65) Prior Publication Data

US 2016/0295086 A1 Oct. 6, 2016

Related U.S. Application Data

(63) Continuation-in-part of application No. 14/923,272, filed on Oct. 26, 2015.

(60) Provisional application No. 62/082,050, filed on Nov. 19, 2014.

(51) Int. Cl.
| | | |
|---|---|---|
| *G16H 80/00* | (2018.01) | |
| *G06T 7/00* | (2017.01) | |
| *H04N 5/225* | (2006.01) | |
| *A61B 1/04* | (2006.01) | |
| *G06F 19/00* | (2018.01) | |
| *G16H 40/20* | (2018.01) | |

(52) U.S. Cl.
CPC ........... *H04N 5/2256* (2013.01); *A61B 1/042* (2013.01); *G06T 7/0012* (2013.01); *G16H 80/00* (2018.01); *G06F 19/321* (2013.01); *G06T 2207/10068* (2013.01); *G16H 40/20* (2018.01); *H04N 2005/2255* (2013.01)

(58) Field of Classification Search
None
See application file for complete search history.

(56) References Cited

U.S. PATENT DOCUMENTS

| | | | | | |
|---|---|---|---|---|---|
| 5,622,528 | A * | 4/1997 | Hamano | ................... | G06F 3/14 348/74 |
| 5,894,322 | A * | 4/1999 | Hamano | ............ | A61B 1/00006 348/65 |
| 6,424,996 | B1 * | 7/2002 | Killcommons | ... | G06F 17/30067 709/206 |
| 6,436,032 | B1 * | 8/2002 | Eto | .................... | A61B 1/00059 600/117 |
| 6,602,185 | B1 * | 8/2003 | Uchikubo | .......... | A61B 1/00041 600/118 |
| 7,957,982 | B2 * | 6/2011 | Omoto | ................ | G06F 21/6245 705/2 |

(Continued)

*Primary Examiner* — Joshua E Rodden

(57) ABSTRACT

A system comprising a network of computers programmed to receive and process visual data transmitted from an endoscopic instrument, display the processed visual data as a live stream and as a set of discrete media objects to be annotated by users of multiple computers accessing the media objects remotely. The endoscopic instrument may feature several buttons arranged for capturing, freezing, and annotating the live stream. The media objects, annotations, and metadata associating the users with the annotations will be embedded by the system into a report using image and text matching algorithms, the report exportably stored and accessed in a patient-physician schedule and database environment.

34 Claims, 14 Drawing Sheets

(56) References Cited

U.S. PATENT DOCUMENTS

| | | | | | |
|---|---|---|---|---|---|
| 8,073,706 | B2* | 12/2011 | Takayama | | G06F 19/327 705/2 |
| 8,125,515 | B2* | 2/2012 | Hibi | | A61B 1/00036 348/65 |
| 8,439,821 | B2* | 5/2013 | Stiller | | G16H 40/20 600/101 |
| 8,554,307 | B2* | 10/2013 | Razzaque | | A61B 6/466 600/424 |
| 2002/0168618 | A1* | 11/2002 | Anderson | | A61F 2/07 434/262 |
| 2002/0175992 | A1* | 11/2002 | Eino | | A61B 1/00048 348/65 |
| 2003/0060678 | A1* | 3/2003 | Watai | | A61B 1/00041 600/109 |
| 2004/0107113 | A1* | 6/2004 | Araki | | A61B 1/00006 600/118 |
| 2004/0131282 | A1* | 7/2004 | Yoshida | | H04N 7/18 382/312 |
| 2004/0151358 | A1* | 8/2004 | Yanagita | | G06F 19/321 382/132 |
| 2005/0075544 | A1* | 4/2005 | Shapiro | | G06Q 10/10 600/300 |
| 2008/0162184 | A1* | 7/2008 | Matsubara | | G06Q 10/10 705/2 |
| 2009/0103836 | A1* | 4/2009 | Shimizu | | A61B 1/00059 382/305 |
| 2009/0307328 | A1* | 12/2009 | Nuttall | | G06F 19/3418 709/212 |
| 2010/0094101 | A1* | 4/2010 | Koike | | G06Q 10/06 600/300 |
| 2013/0152020 | A1* | 6/2013 | Nishiyama | | A61B 1/00009 715/835 |
| 2013/0185096 | A1* | 7/2013 | Giusti | | G06Q 50/24 705/3 |
| 2013/0293694 | A1* | 11/2013 | Mizobe | | H04N 7/183 348/77 |
| 2014/0258918 | A1* | 9/2014 | Morishima | | A61B 6/463 715/783 |
| 2014/0374476 | A1* | 12/2014 | Ban | | G06Q 30/02 235/375 |
| 2016/0012195 | A1* | 1/2016 | Lee | | G06Q 50/24 705/3 |
| 2018/0039733 | A1* | 2/2018 | Golay | | A61B 6/14 |

* cited by examiner

SYSTEM FOR ENABLING REMOTE ANNOTATION OF MEDIA DATA CAPTURED USING ENDOSCOPIC INSTRUMENTS AND THE CREATION OF TARGETED DIGITAL ADVERTISING IN A DOCUMENTATION ENVIRONMENT USING DIAGNOSIS AND PROCEDURE CODE ENTRIES

PRIORITY CLAIM

This application is a continuation-in-part of U.S. patent application Ser. No. 14/923,272, filed on Oct. 26, 2015, which, in turn, claims the benefit and priority of U.S. provisional patent application 62/082,050, filed Nov. 19, 2014. The above referenced applications are incorporated herein by reference as if restated in full.

BACKGROUND

Physicians currently are challenged by the inadequacy and lack of existing instrument focused computer systems that enable peers to participate in the diagnosis of patient maladies in a procedure environment. The present application seeks to solve this problem by providing a system in which instruments and computer systems are connected in a network enabling multiple remote physicians to be virtually present during procedures.

SUMMARY

The embodiments of the invention described herein pertain to an endoscope image capturing and annotation system. In one embodiment, the system includes an endoscope coupled to a light source, and a computer system. The endoscope may feature a probe section, a handle, and a cable connecting the endoscope to a processor of the computer system. The light source may be provide light through the probe section, or in a separate probe that is substantially attached and guided by the endoscope probe, and configured to be aimed in the direction chosen by the physician or operator of the endoscope portion of the system.

The endoscope is configured to transmit visual data by means of a digital camera. The images accessed by the endoscope may be digitized within the endoscope portion of further down the line in an analog-to-digital converter. The computer system receiving the visual data may comprise a processor engaged with computer storage memory for receiving data and instructions and for storing data. The processor may be equipped with input devices such as a keyboard and mouse and a display device such as a monitor. The computer system may also be connected to a network of computers and/or computer systems, permitting cooperative work on the images, annotating, and reporting. Each computer system may be identified using a unique identification number. Each user may be assigned a unique username.

In one embodiment, the user may communicate and the processor may receive a launch procedure instruction. This launch procedure instruction may be communicated by pressing a button or switch on the endoscope or by selecting a button on a user interface portion of the system. This communication initiates a procedure session for the system, during which the time may be tracked for the purposes of record keeping. A procedure window may be displayed on the user interface on the display device, which will permit a visualization of one or more facets of the procedure, as captured using the endoscope or similar medical device and commented upon by the physician. Visual data may be captured from a view portion of the endoscope using a physical capture button located on the endoscope or through the use of a physical button connected to but not rigidly fixed to the endoscope, such as a foot pedal. The visual data may be transmitted to the processor, converted to display data, and displayed as a live stream in the procedure window. Once a selection of the display data is "captured", it is effectively saved, either as a single image or as a video consisting of multiple frames and treated as a captured media object. Media objects captured in this way may be saved to a gallery section, generally identified by the time, date, and name of the operating physician, name of the patient, and point in time captured during the procedure.

Users of other computer systems may request to join the procedure, permitting them to view the display data of the live steam, as well as the captured media objects. They may also be able to make remarks in a remark section that would be visible to the physician during the procedure. Live footage of the other users, captured via webcam-like instruments, may be displayed on the display screen used by the operating physician as well, for the purpose of communicating helpful advice, suggestions, or instructions. The request to join the procedure is effectively a request to view the procedure as documented in the procedure window. The request may be activated by the entering of a code created by the operating physician or assigned by the system to the procedure. If the request is accepted, the procedure window may be displayed on the requesting user's display devices.

The operating physician may communicate and the system may receive an annotation instruction, preferably using a keyboard and mouse combination but it is also conceivable that this communication may be made by voice and received by the system via a microphone. Once this communication is received, the system may display an annotation window featuring thumbnails of captured media objects. These thumbnails may be selected and the media objects may be viewed in turn. Graphical positions on the media objects may be selected by the user by clicking or otherwise identifying them graphically on a frame of a media object. Once a graphical position is identified, the system will provide an annotation field that may be entered with text by the user. The identity of the user and/or the identification of the computer being used when making the entry may be attached as metadata either to the media object directly or on a report in which the media objects are themselves attached or associated by the system. Annotation request may be also made by other users using other computer systems. These requests may be merged with the view requests or may require separate and distinct identification and acceptance procedures. Once annotations are made on a media object on one computer system, they will also be transmitted to and displayed on other computer systems and display devices operated by accepted users. In one version, annotations will be uniquely displayed by color, shape, text, symbol, or ID, to identify and distinguish the user making the annotation.

DETAILED DESCRIPTION

Figure 1:
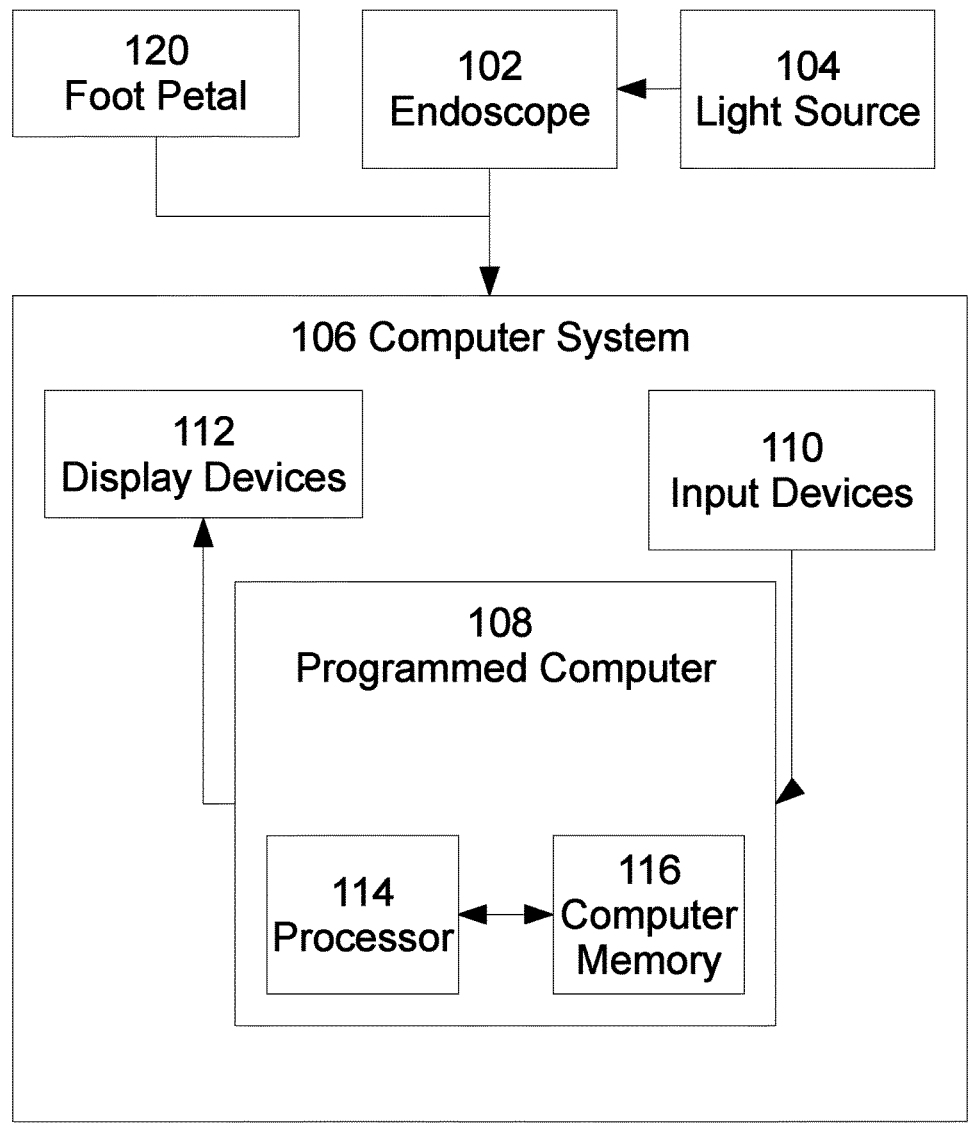
FIG. 1 shows an exemplary computer system.

As shown in FIG. 1, the system may comprise an endoscope 102 connected to and receiving light from a light source 104, and connected to a computer system 106 comprising one or more programmed computers 108, one or more input devices 110, and a display device 112. Each programmed computer may comprise a processor 114 engaged with a computer memory 116 to execute instructions loadable onto and then provided by the computer memory. The computer system may be connected to a network comprising other computer systems. In one embodiment, the system may also comprise a foot pedal 120 connected to the computer system. The foot pedal may be connected to a processor via a USB cable. The input devices may include a keyboard, a mouse or cursor controller, and/or a microphone. In one embodiment, the endoscope may comprise a freeze button and/or a capture button. In another embodiment, the system may comprise a time tracker, which tracks the time a user spends using the platform, or discrete parts of the platform such as particular pages therein. This information is helpful in providing accurate information for billing purposes.

The system may comprise a software application or platform that may be operated in the form of a desktop application or a web application accessed through a browser. The application may comprise a landing page, featuring fields for a user name, a password, and a clinic ID. The fields must match data from a database in order for the user to access the platform. Otherwise, access will be denied by the application.

The platform may comprise a scheduler, a calendar, a patient search, and an inbox. The scheduler may comprise a database in which appointments are organized by a time slot, a patient name, a physician name, and other relevant parameters. The scheduler may be graphically displayed on a scheduler page as a chart with a time column, a name column, and columns for other relevant parameters. Each row in the time column may represent a time slot and may be linked to the patient search.

The patient search may feature a first window with a list of patients and a search field. After enterting a name or relevant parameter in the search field, the search terms are searched within their respective categories in a patent database, and a list of patients matching the search terms will be displayed in the first window. By selecting a patient on this list, an appointment in the selected time slot is created and the patient's name and other parameters are displayed in the chart.

Figure 2:
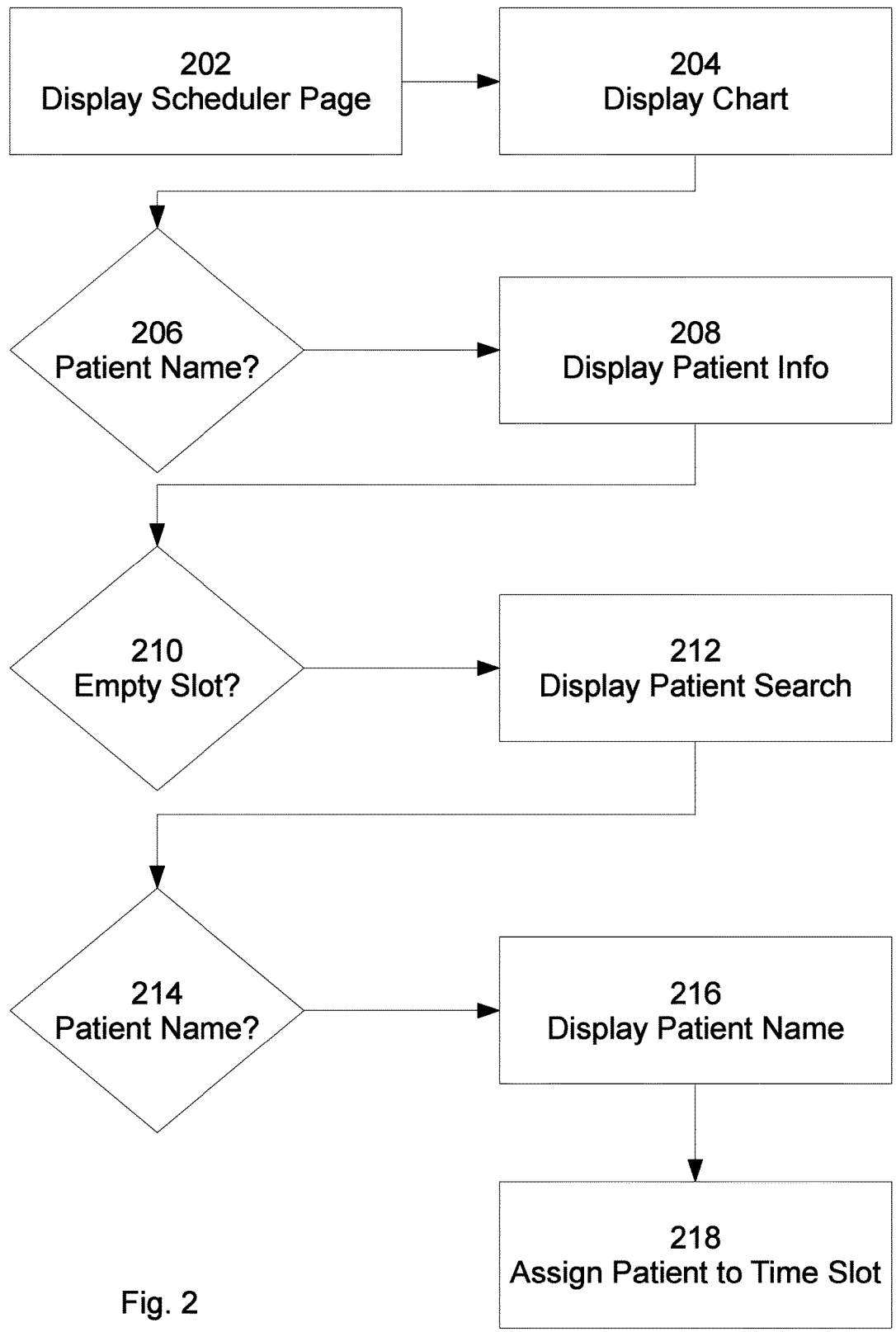
FIG. 2 is a flowchart of an exemplary process.

As shown in FIG. 2, the system may graphically display the scheduler page 202. On the scheduler page, the system may graphically display the chart 204, the chart comprising at least a time column and a name column. If the system receives a user selection of a patient name in the name column 206, the system will display patient information 208. If the system receives a user selection of an empty slot in the name column 210, the system will display the patient search page 212. If the system receives a user selection of a patient name on the patient search page 214, the system will display the patient name in the selected time slot 216 and assign the patient to the time slot in line with the selected empty slot 218.

Figure 3:
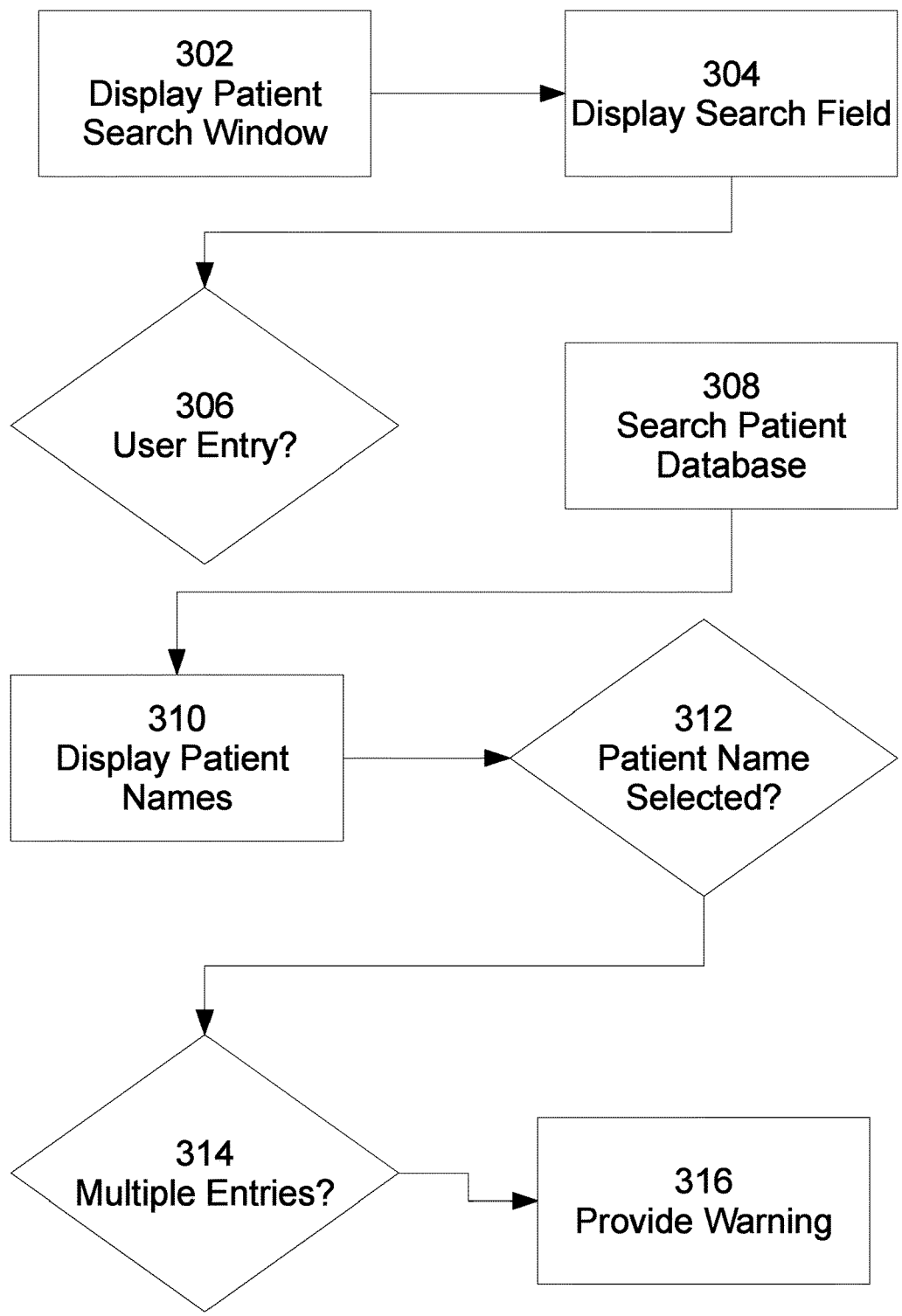
FIG. 3 is a flowchart of an exemplary process.

As shown in FIG. 3, the system may graphically display a patient search window 302. The system may display a search field in the patient search window 304. If the system receives a user entry in the search field 306, the the system will search the patient database 308, and display patent names 310 associated with parameters, including the name, that matches the terms entered by the user.

Figure 3A:
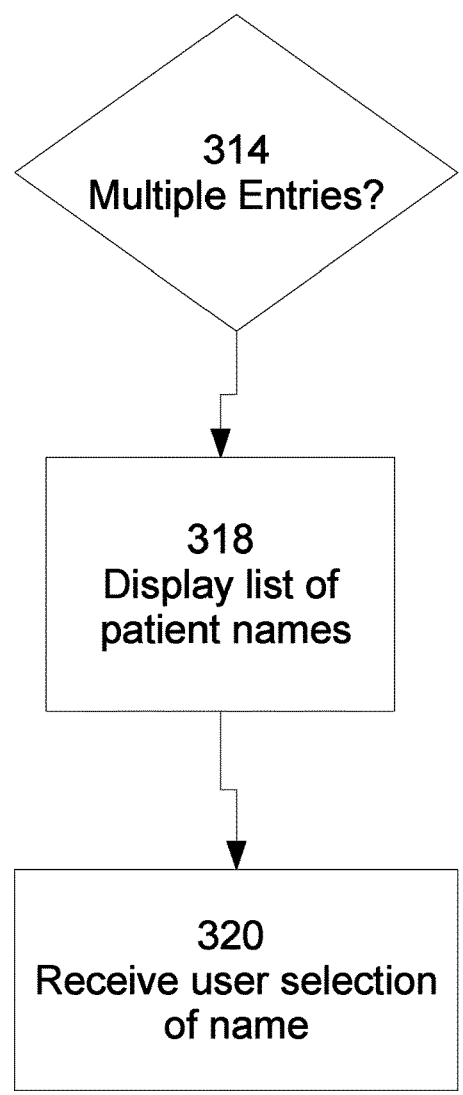
FIG. 3a is a flowchart of an exemplary process.

In one embodiment, if a patient name is selected 312, but there are multiple entries for that patient name 314, the system may provide a warning to a user 316. In another embodiment, as shown in FIG. 3a, if there are multiple entries for the patient name 314, the system may display the list of identical or near-identical patient names with one or more other parameters 318, allowing the user to select the specific patient entry in the group of identical or near-identical patient names which the user intends to enter for the appointment 310.

The patient search may also feature an add patient functionality. By selecting an add patient button, patient parameter fields will be displayed, including first name, last name, ssn, dob, gender, email, etc. When these fields are entered and the new patent is added to the database, then the patient's name and other parameters are added to the patient database and in addition, added to the scheduler for the selected time slow.

In one embodiment, if a name entered using the add patient functionality is identical to a name already in the patient database, the system may alert the user that the name constitutes a duplication.

In one embodiment, the system may automatically merge multiple patient information entries if one or more parameters are identical, such as the social security number. In another embodiment, the system may provide a merge button or may offer a drag and drop feature allowing a user to command the system to merge two patient entries by selecting two patient entries and then selecting the merge button, or drag one patient entry onto another patient entry.

Other parameters in the scheduler may relate to the appointment. These parameters include the name of the doctor, the referring physician, the duration of the appointment, the start time and end time of the appointment, as well as remarks. In one version, the identification of the instrument being used may be added.

The chart on the scheduler page may also feature a procedure column. This column feature a launch procedure button for each appointment. When this launch procedure button is selected, the system will display a procedure page. In one embodiment, the application will begin timing the duration during which the procedure page is open for the user. In one embodiment, multiple users may simultaneously and remotely access the procedure page for the same procedure at any given time. The application may differentiate between the user that launched the procedure and the one or more users that are accessing the launched procedure. The application may receive data from one or more input devices connected to the processor used by the user who launched the procedure but deny data from one or more input devices connected to the processors of other users. The application may transmit data to the processors used by the other users.

The procedure page may feature a start button. When the start button is selected, the endoscope begins to capture visual data and transmits it to the processor. The visual data is transformed by the system into a live stream, which is displayed in a first window. The procedure page may also feature an end button. When the end button is selected, the endoscope ceases capturing and transmitting visual data.

The procedure page may feature a capture button. When the capture button is selected, the current image in the live stream is captured and displayed in a second window. In one version, the current image may be captured by pressing on the foot pedal. In another version, the current image may be captured by pressing the capture button on the endoscope. In yet another version, the functionality provided by the capture button may also be initiated through voice command. In this version, the system comprises a microphone for receiving voice commands.

Figure 4:
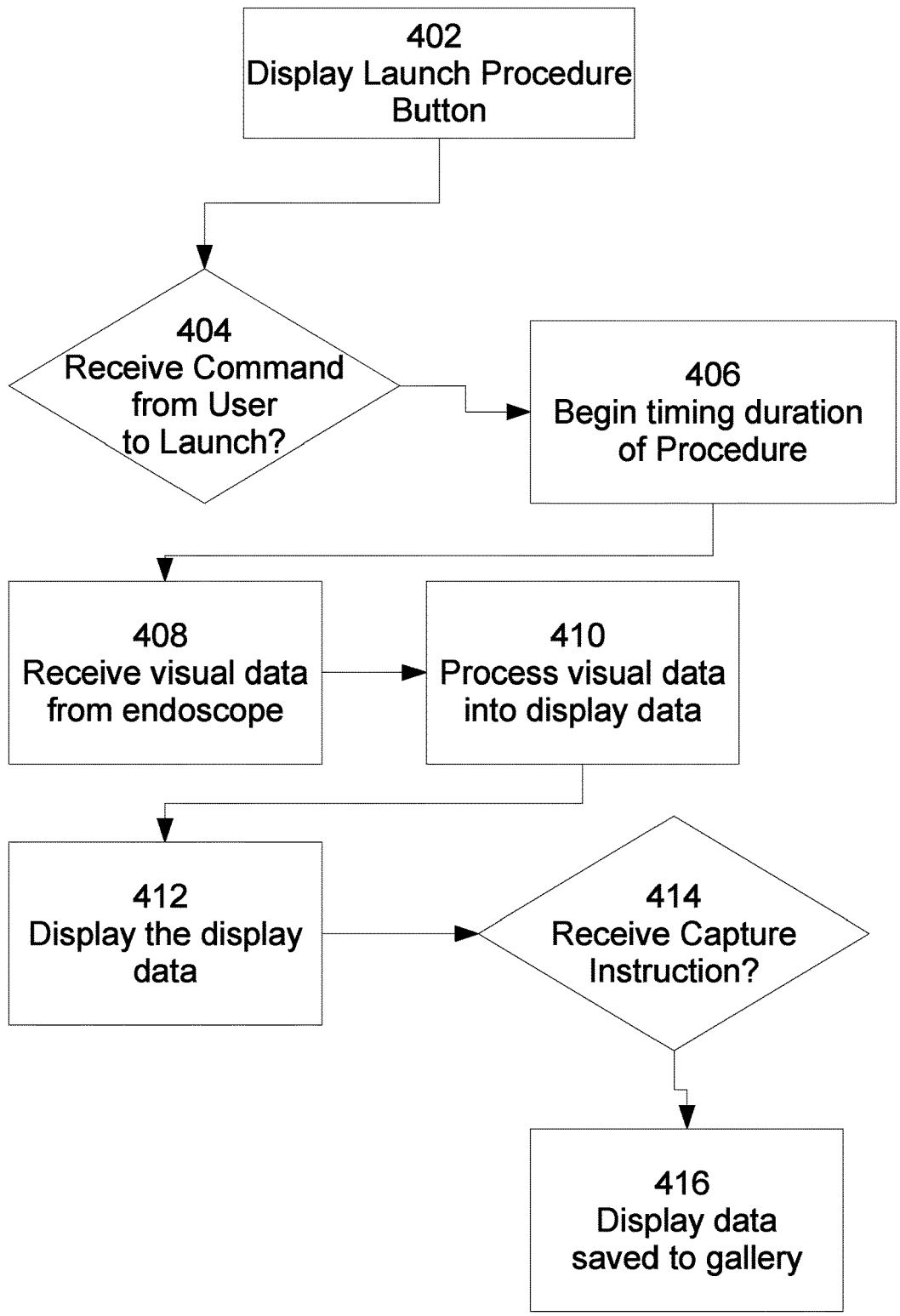
FIG. 4 is a flowchart of an exemplary process.

As shown in FIG. 4, the system may display a launch procedure button 402. If the system receives a command from a first user to launch a procedure 404, the system will begin timing the duration of the procedure 406. The system may receive visual data from an endoscope 408, process the visual data into display data 410, and display the display data in a first window 412. If the system receives a capture instruction from the user 414. the display data is saved to a thumbnail gallery 416.

Figure 4A:
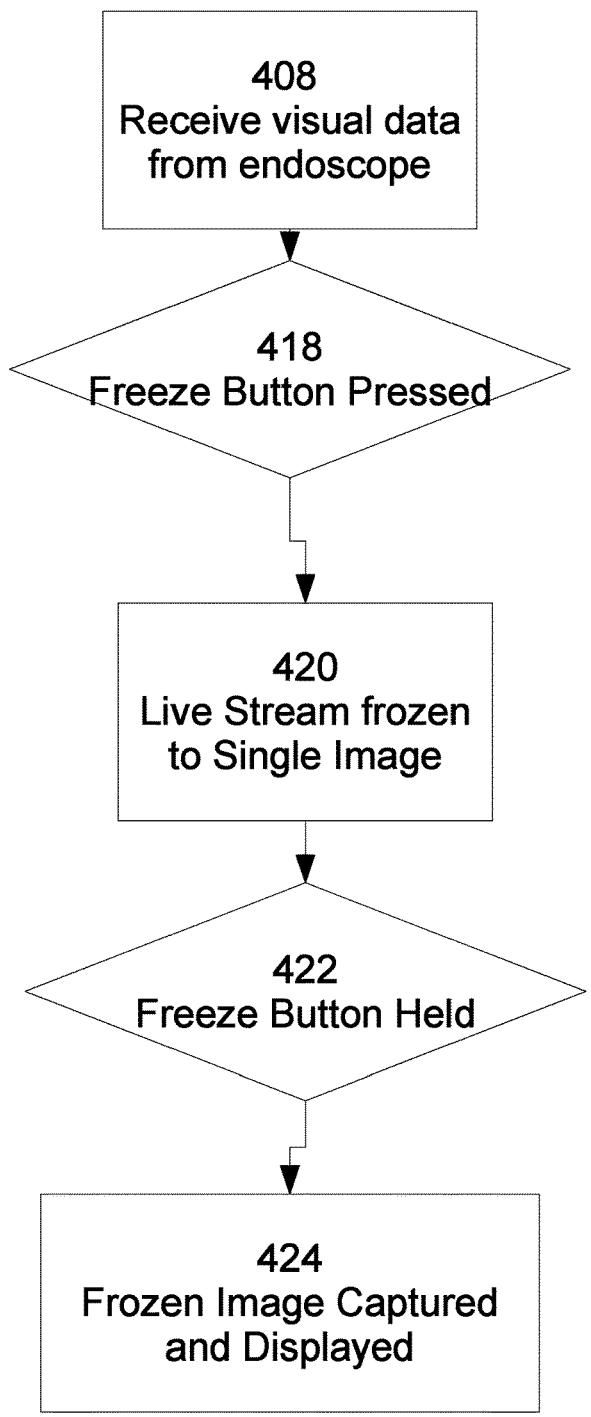
FIG. 4a is a flowchart of an exemplary process.

In one embodiment, as shown in FIG. 4a, when the system receives visual data from the endoscope 408, a live stream in the first window is frozen to a single image 420 if the freeze button on the endoscope is pressed 418. In one version, if the freeze button is pressed and held or maintained for a predetermined duration or a duration selected by the user, or if a freeze instruction is received 422, then the frozen image is captured and displayed in the second window 424. In another version, the frozen image is only captured and displayed in the second window if the image is frozen for a predetermined duration or a duration selected by the user.

In one embodiment, a video sequence of the live stream can be captured by pressing and/or holding the capture button on the procedure page, the capture button on the endoscope, or the foot pedal, and pressing/or releasing the same once the desired video length is captured.

The procedure page may feature an annotate button. When the annotate button is selected, the platform may display an annotation page, feautring thumbnails of the images and videos captured during the procedure. In a first window, one of the captured images or videos is displayed. If a thumbnail of a different captured image or video is selected, then that image or video is displayed in the first window. A graphical position on an image or video in the first window may be selected, which creates an annotation field adjacent to or directed to that graphical position. Text may be entered into the annotation field via an input device, such as a keyboard, or may be received via voice, which is mediated by a voice-to-text program. The annotation field may comprise a drop down menu with a pre-populated vocabulary. If a video is being annotated, then the annotation may remain in the position based on a graphical border placed on a graphical representation of a time track. In one embodiment, the platform uses image recognition to identify the borders or position of the object annotated in a video, and the annotation will track or follow the object as it moves throughout the video.

Figure 5:
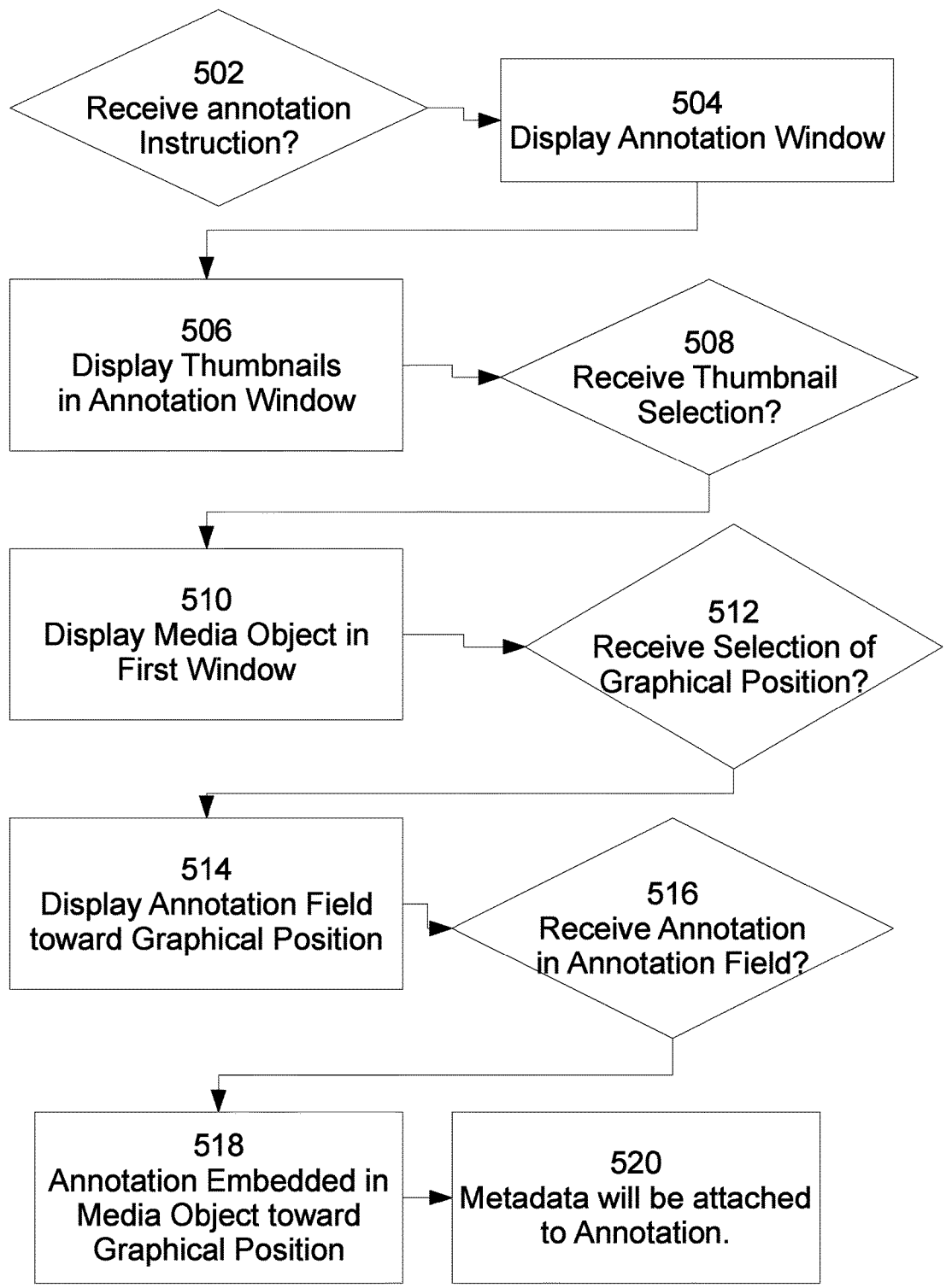
FIG. 5 is a flowchart of an exemplary process.

As shown in FIG. 5, if the system receives an annotation instruction from a user 502, the system may display an annotation window 504. One or more captured media objects, such as images or videos, are displayed as thumbnails on the annotation window 506. If a thumbnail is selected by the user 508, then the media object represented by the thumbnail is displayed in a first window 510. If the system receives a selection of a graphical position in the first window 512, the system will display an annotation field adjacent to or directed toward that graphical position 514. If the system receives an annotation entered into the annotation field 516, the annotation will be embedded in the media object 518. Metadata, including the username or ID of the annotating user, will be attached to the annotation and/or media object 520.

In one embodiment, annotation may occur via a single click and drag action. The object of the annotation is selected by the single click, and the drag creates a line that features a head which points to the object on one end, and on the other end, a text field into which text can be entered.

In another embodiment, the color, font, size, and modification of text may be achieved by acting on a typical text editing window that appears on the relevant page. In one version, it may also be achieved by keyboard commands and/or a combination of left and right mouse clicks.

In yet another embodiment, the thickness, length, color, and multiplicity lines may be achieved through similar actions. Multiple lines may be drawn from a single object in image or video to multiple annotations fields. Also, multiple lines may drawn from a single annotation field to multiple objects in image or video.

The annotation page may also feature a delete button. If a thumbnail is selected and then the delete button is selected, the image or video represented by that selected thumbnail is deleted or otherwise removed from the procedure. The annotation page may also feature a save button.

When an annotation is made, metadata is stored by the platform identifying the username or id of the annotating user, the time spent by the user in viewing or using certain pages of the platform, and the dates.

If the save button is selected, then all of the media objects, including images and/or videos captured during the capture session, as well as the annotations embedded in the media objects, are saved to a remote server and/or a local computer.

The report page may feature a template list. Once a template is selected from the template list, the report page may display a template in a first window, featuring a category and a field adjacent to the category. When the field is selected, a tree of terms is displayed in a second window. The collection of terms may be specific to the template selected, and each template may be tailored to medical practice areas or even for specific procedures. When a term is selected from the tree of terms, the term populates the field in the template. The tree comprises parent nodes and child nodes. If a child node is selected, then the field may also automatically populate the parent node in addition to the child node. If multiple terms are selected, those multiple terms will populate the field. In one embodiment, the terms populating the field are entered and displayed in a manner organized by the platform based one or more logic relationships handled by the platform. In another embodiment, text can be entered directly into the field by the user using an input device such as a keyboard. This "free text" can be placed before, after, or in-between terms derived from the tree of terms. Text can also be placed outside of the field. In yet another embodiment, text can be entered via an audio input device and a voice-to-text dictation program, which may be internal or external to the system.

Figure 6:
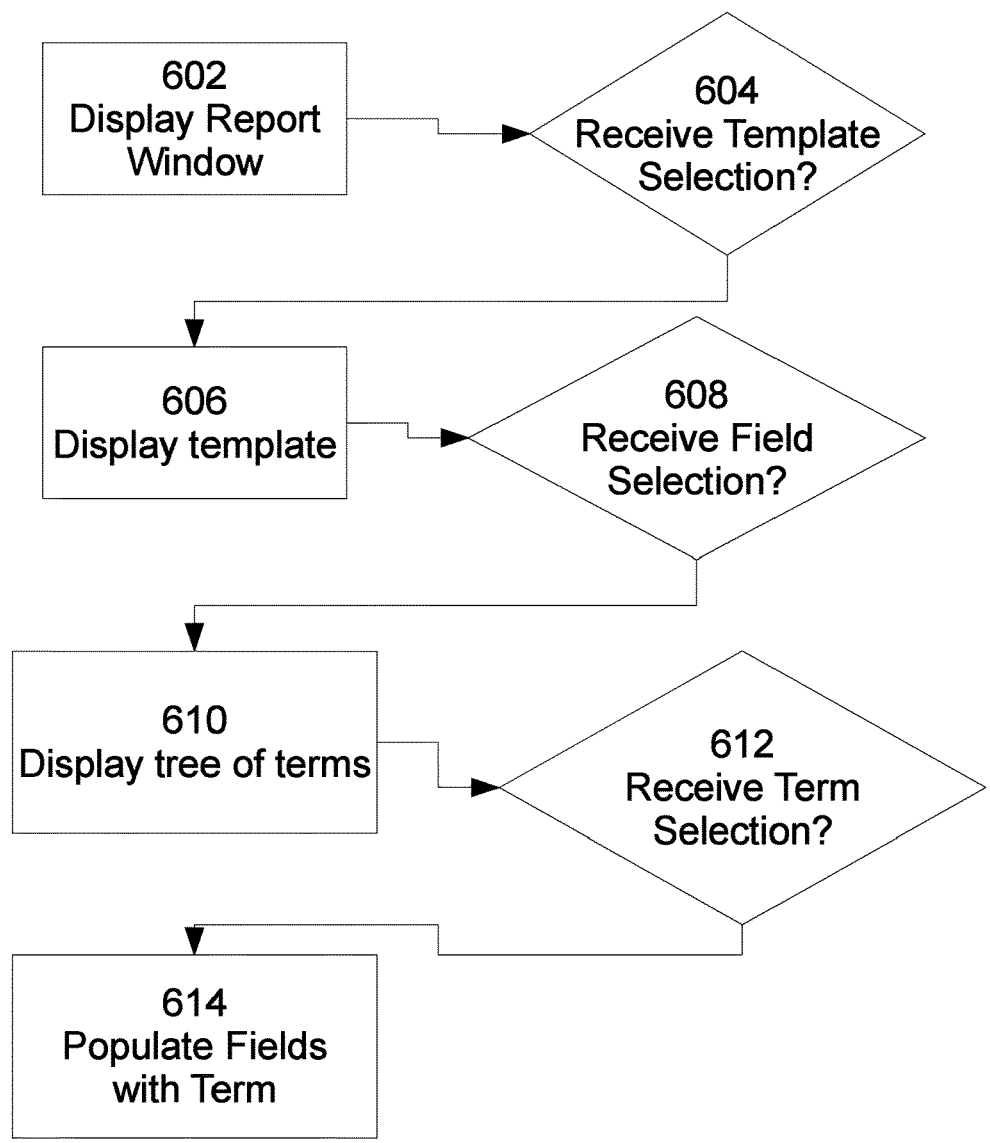
FIG. 6 is a flowchart of an exemplary process.

As shown in FIG. 6, the system may display a report window with a list of templates 602. If the user selects a template 604, the system will display that template in a first window 606. If the user selects a field 608, the system will display a tree of terms in a second window 610. If the user selects a term from the tree of terms 612, the system will populate the field with the term 614.

In one embodiment, several trees IDs are provided and the user can select the tree IDs he or she wishes to be used to populate the second window. In another embodiment, users will be provided by an administrator or the system itself a list of template sections, each template section consisting of one or more different template pattern types. The user can select the template pattern type for each section that he or she wishes to be included in an ultimate template. This is the configuration and personalization process and may proceed regular usage of the system.

Figure 7:
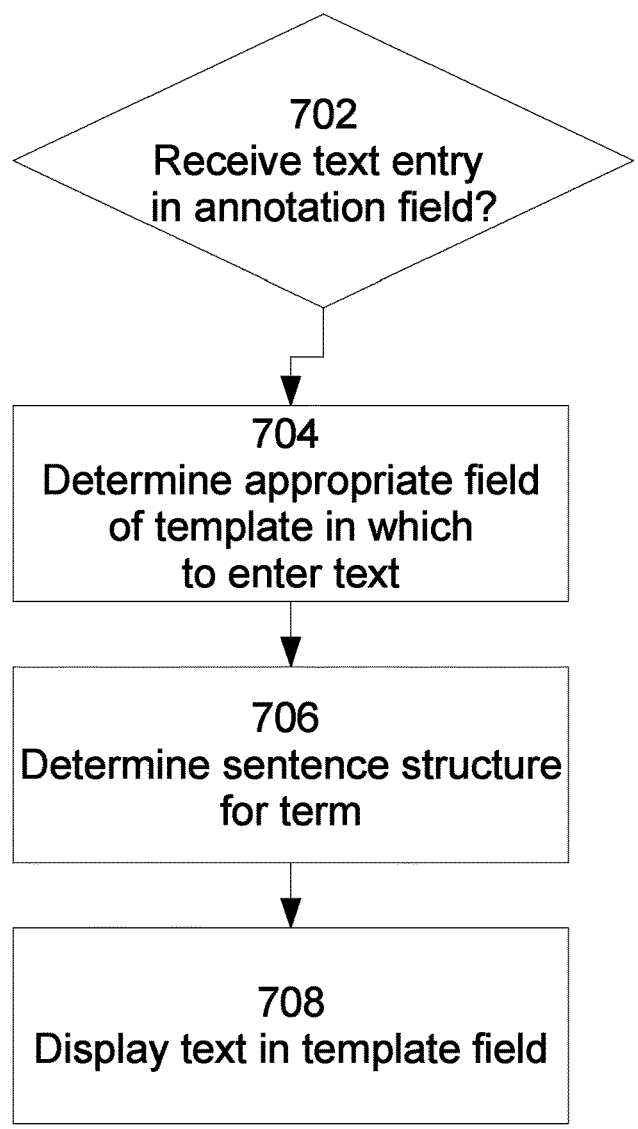
FIG. 7 is a flowchart of an exemplary process.

In one embodiment, as shown in FIG. 7, if the system receives text entered into the annotation fields on the annotation page 702, it may be displayed in the template 708. The text can be combined into sentences 706 and displayed in the appropriate section of the template 704 based on context, such as other text that is entered in the annotation fields, based on image recognition, or based on the anatomic site as entered by the user. The sentence structure may be determined using a pre-determined sentence structure assigned to each category or field in the template.

If a diagnosis term is entered in an annotation field for a first image, and an anatomical area is entered in another annotation field for the first image, then in the report section, the diagnosis may be listed adjacent to the anatomical area. If a given diagnosis associated with a given anatomical area is described by an ICD code, that code is also displayed in the report in a diagnosis field. If a procedure term is entered in an annotated field, then in the report section, a procedure may be listed adjacent to or within a procedure field.

Figure 8:
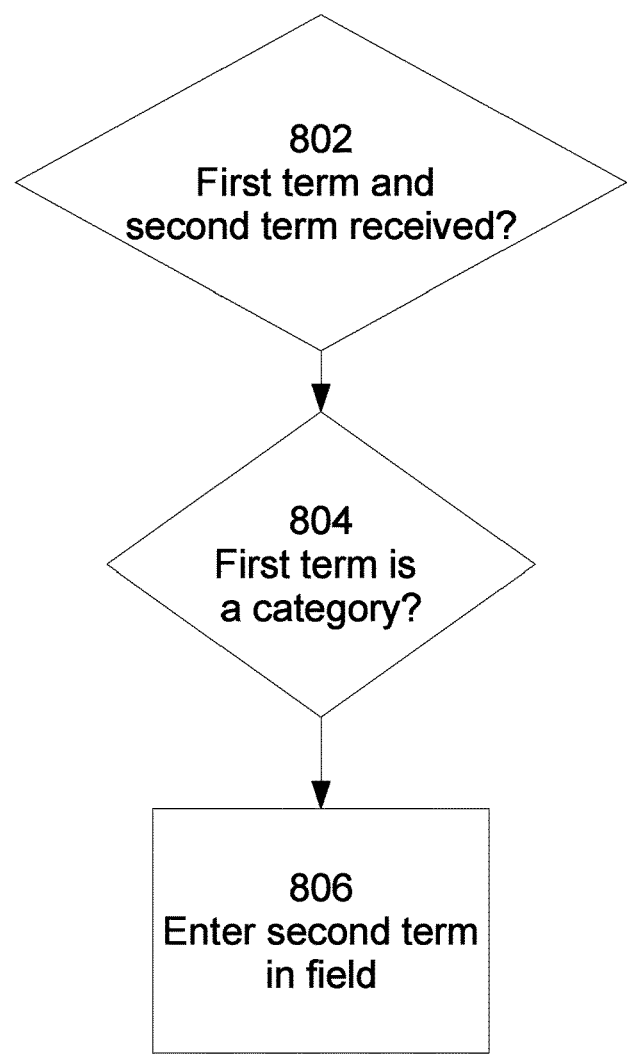
FIG. 8 is a flowchart of an exemplary process.

As shown in FIG. 8, if a first term and a second term are entered in an annotation session 802, and the first term is a category in a template 804, then the system will enter the second term in the field adjacent to the category 806. The first term, which is comprised of text, may be analyzed for its textual equivalence to the category, which is also comprised of text. The textual equivalence may lie in a predetermined identicality of letters, or in a synonymous relationship predetermined by the system or assigned by a user or operator. One example of a category is "Biopsy". If Biopsy is entered as a first term and an anatomical location, such as "colon" is entered as a second term, then the field of a Biopsy category on the template will be filled with the term "colon".

Figure 9:
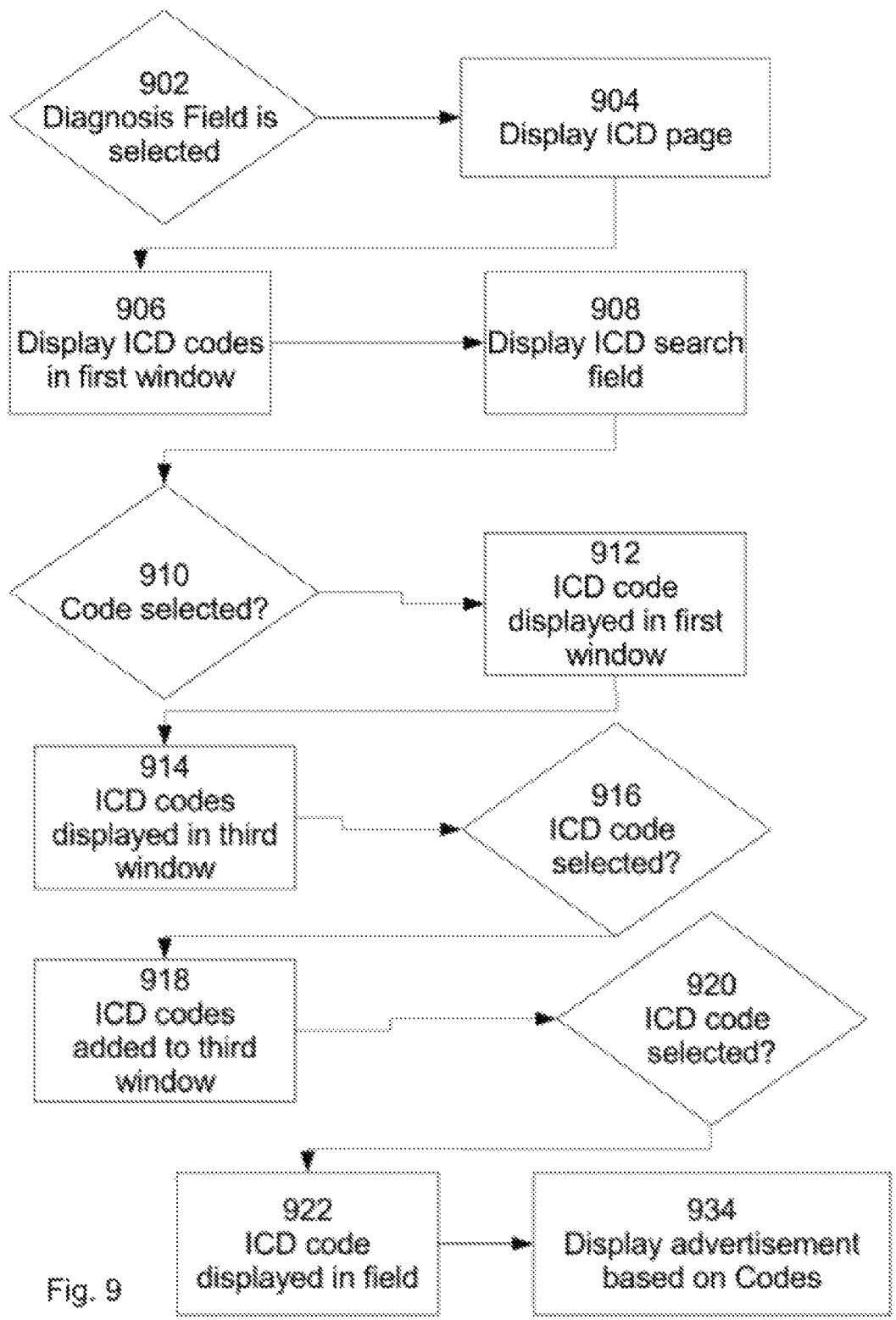
FIG. 9 is a flowchart of an exemplary process.

As shown in FIG. 9, if a diagnosis field is selected by a user 902, the system displays an ICD page 904. A first window is displayed on the ICD page, with a list of ICD codes displayed in that first window 906. A second window features a search field for searching a database of ICD codes and an area where results are displayed 908. If an ICD code is selected from the results 910 and added to the first window by dragging and dropping an ICD code from the second window to the first window, or by selecting an ICD code in the second window and then selecting an add button, then it is displayed in the first window 912. A third window displays a list of ICD codes that are relevant to the template 914. ICD codes can be added to the third window 918 by selecting an ICD code from the first or second window and then selecting an add button 916, or by dragging and dropping an ICD code from the first or second window to the third window. The procedure field operates very similarly to the diagnosis field, except that instead of ICD codes, there are procedure codes, such as CPT. If an ICD code is selected from the third window by the user, 920, the system will display it in the diagnosis field of the template 922, and then display an advertisement based on the codes 934.

Figure 9A:
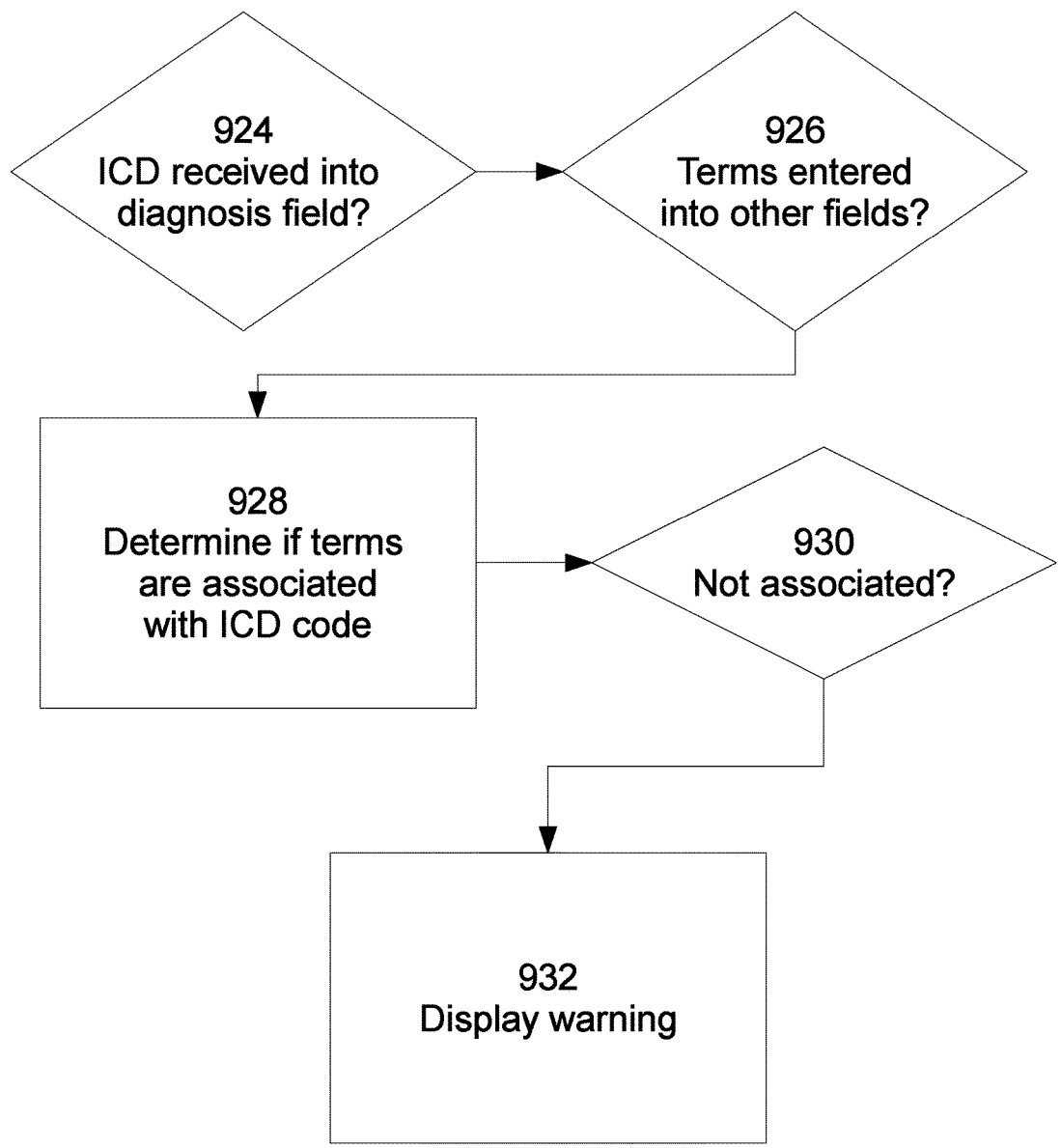
FIG. 9a is a flowchart of an exemplary process.

Each code may be associated with one or more terms from the tree of terms. In one embodiment, as shown in FIG. 9a, if an ICD code is entered into the diagnosis field 924, and if terms are entered into other fields 926, the system will determine whether the terms are associated with the ICD code 928. If they are not associated 930, then a warning will be displayed alerting the user that the code entered is not adequately supported by the other terms entered 932.

In one embodiment, the diagnosis codes, procedure codes or CPT codes entered by a user may be used to target advertising toward that user. The system may display banner ads based on the procedure codes or CPT codes used 934. This may function as CPT narrowcasting advertising.

Figure 10:
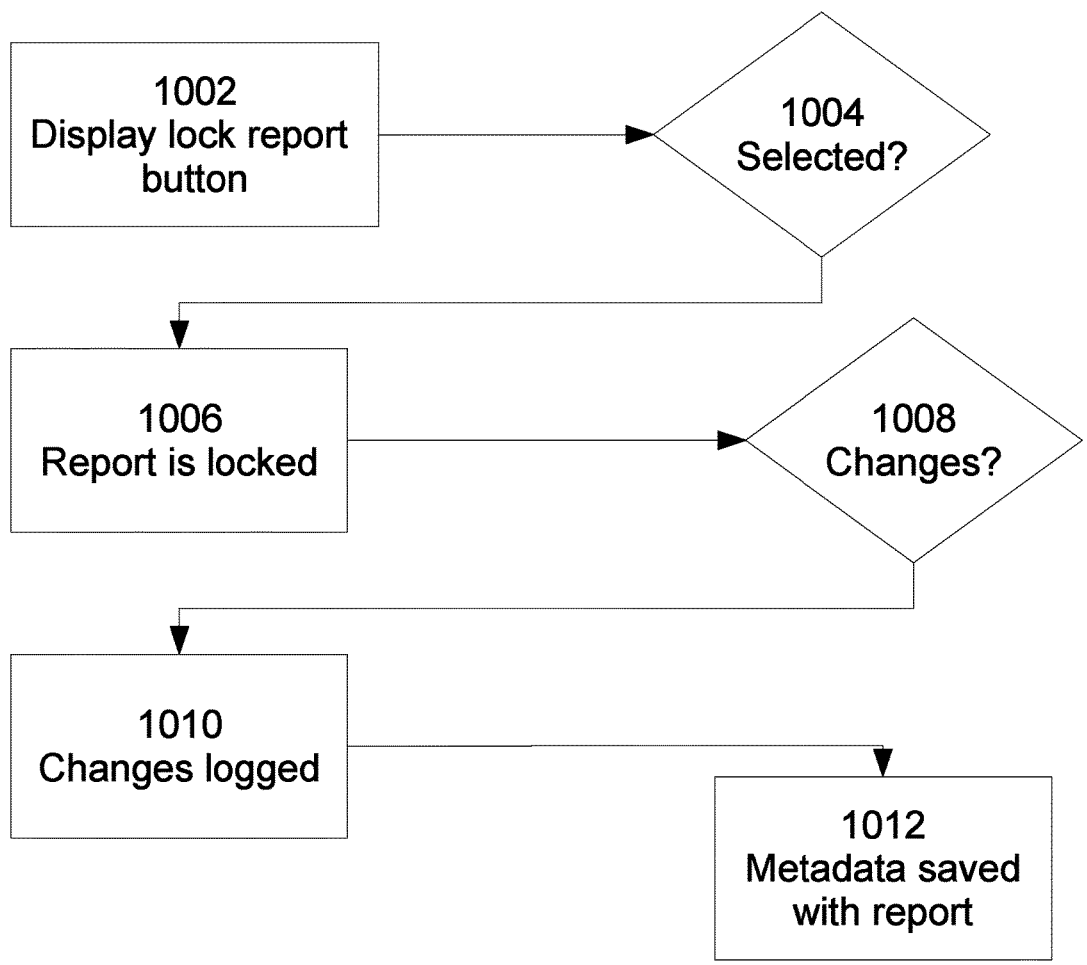
FIG. 10 is a flowchart of an exemplary process.

As shown in FIG. 10, the report page may feature a lock report button 1002. If selected, 1004 the report as manifested by the template and its terms, is locked or finalized 1006. If any changes are made after the report is locked 1008, they will be logged 1010, with the logged information including the changes and the time and date of the changes and the user name of the user making the changes, saved as metadata associated with the report 1012.

Figure 11:
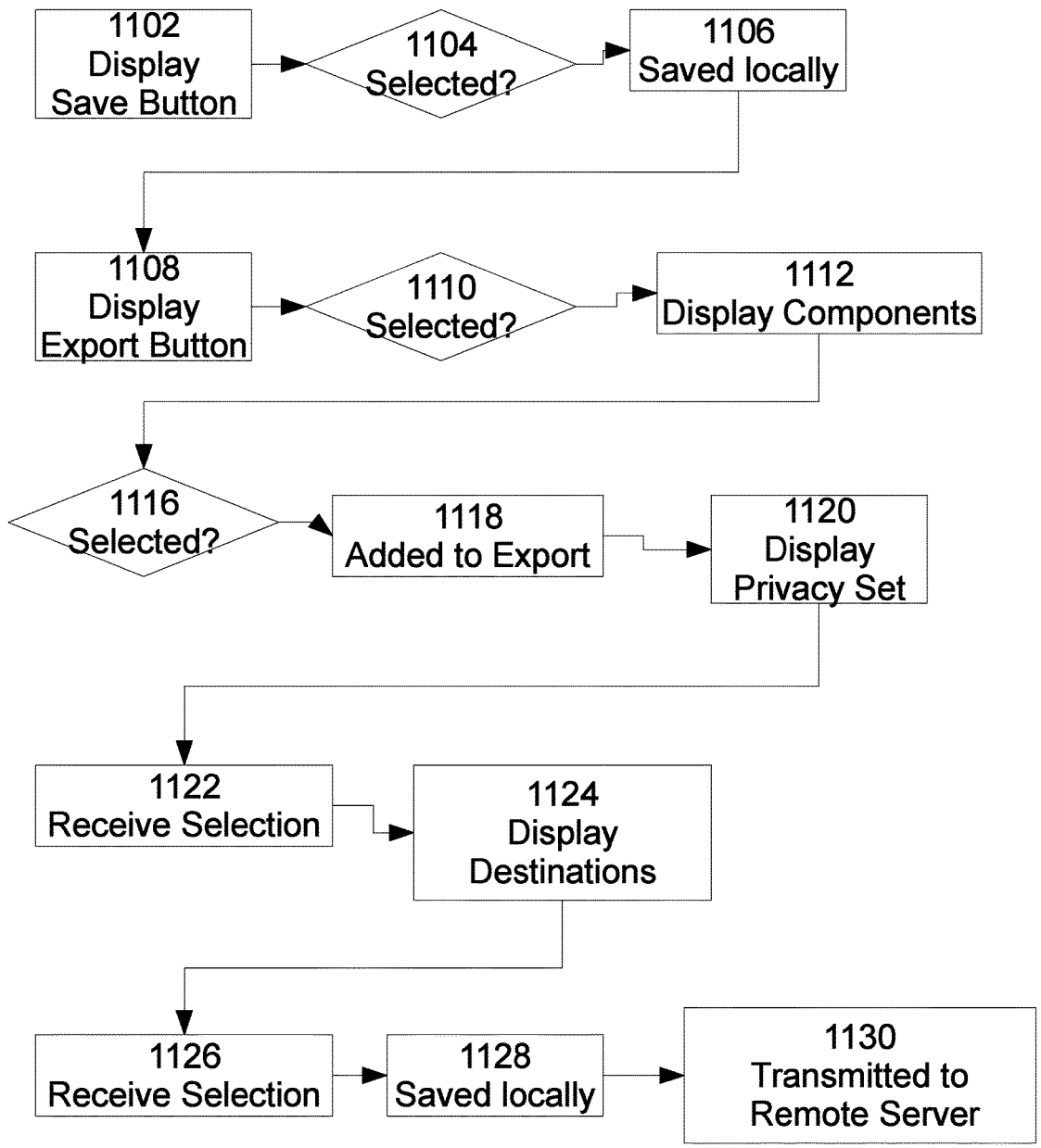
FIG. 11 is a flowchart of an exemplary process.

As shown in FIG. 11, the report page may feature a save button 1102. If a selection is received from the user 1104, the report is saved to a local storage 1106. The report page may also feature an export button 1108. If selected 1110, the report page may display a list of components 1112 of the report to be exported. If a component is selected 1116, it will be added to an export file 1118. The report page may feature a privacy set 1120, which permits the user to select whether identifying patient information is to be added to the export file 1122. Information may be sent in two privacy forms: in the first, the information may have the patient identification information attached, and in the second, the information may be stripped of the patient identification information.

The report page may display a list of destinations to which the report may be transmitted, including a pathology center and/or any other medical centers 1124. One or more destinations may be selected by the user 1126. Export may be internal to the system, such that the report will be transmitted to the platform inbox of the designated recipient, or it may be external to the system, such that the report may be sent to a designated email address. The report may be exported as a pdf or any other appropriate form. The report will also be embedded with the images and/or videos captured and annotated during the procedure based on the components selected. Information entered into the system may be stored locally 1128 prior to transmitting the information to a remote server 1130.

In one embodiment, all information entered into the system, including procedural information, images, and reports, will be stored locally and then transmitted to a remote server. The transmission to the remote server may be initiated based on a predetermind time cycle, such as every week, day, or hour, or after an event, such as the selection of one or more buttons or commands made by the user. The transmission may also be achieved manually, through an explicit command from the user.

The platform may comprise an image and/or video archive, a visitation archive, an insurance archive, a procedures archive, an addresses archive, and a bill archive. These archive may be limited to a selected patient and may be linked to the patient's profile.

The system may provide a report making functionality that organizes the data in the database, including patient, procedure, and diagnosis parameters and displays it in the form of one or more charts and graphs. The data may include text as well as images taken during procedures. Images may be juxtaposed adjacent to text data. Images may also be grouped together and displayed based on search parameters entered into a search field.

A search button may be displayed on or adjacent to images or videos captured during a procedure. The system may respond by displaying other images and descriptions of those images based on computer image recognition.

The images and/or videos in the image/video archive may be organized by date. The archive may comprise a list of dates. Each date may be selected, revealing thumbnails of the images and/or videos captured on those dates. An individual thumbnail may be selected to expand the size of the image. Multiple thumbnails may be selected so that the images and/or videos may be compared side by side.

In one embodiment, information relating to ICD, CPT codes, treatment choices, medication, and other physician-patient generated data, is transmitted to a central database from multiple physician terminals. This information may be scrubbed of patient identification data, rendering the data anonymous. Aggregate data may then be requested from and transmitted to a third party for use in statistical, academic, governmental, and industrial use. The aggregate data may be prepared into reports by the system prior to such transmission.

Embodiments of an invention relate to an office management system. Aspects include a patient database, means for creating appointments for the patients, and a calendar to organize and display the appointments. Other aspects include means to add information to a patient's file, including photographs, procedure history, etc.

In one embodiment, the Office Management Tool comprises a scheduler means for organizing appointments. This means may include a link to a separate page, a drop down menu, a spoke on a hub and spoke, or an expandable/collapsible pane, panel, or cell.

In one embodiment, the scheduler comprises a calendar means for indicating what appointments are scheduled and how many are scheduled for a given date. This means may include a link to a separate page, a drop down menu, a spoke on a hub and spoke, or an expandable/collapsible pane, panel, or cell. The current date, which is the date that matches the real world calendar date, may be displayed in one color, while the date selected by the user may be displayed in another color.

In one embodiment, the each day displayed on the calendar is also a clickable or otherwise actionable; when the link for a given day is selected, the user interface displays the Time Slots for that day, which will be described later.

In one embodiment, the calendar may be scrollable or similarly actionable, so that a user may access a prior or subsequent month by clicking arrows pointing hither and thither or dragging a button from one side of the Calendar to another. In one embodiment, the Calendar becomes visible when a Calendar Icon is selected, and hidden when that Calendar Icon is selected again. In another embodiment, the number of due dates scheduled for a certain date appear on that date in the Calendar.

In one embodiment, the Scheduler features a Time Slots display. In one embodiment, the Time Slots display features a list of time increments, such as one hour increments, half-hour increments, etc. In this embodiment, the increments are fixed and cannot be changed by the user. In another embodiment, the user can select the time intervals he or she wishes to use to view the appointments for a given day.

In one embodiment, the Scheduler features an Add Appointment button. When this button is selected, a drop down or accordion menu opens, featuring fields. These fields may include the name of the patient, the name of the referring physician, the date of the appointment, the start time of the appointment, the end time of the appointment, the status of the appointment (whether it is complete or not), the phone number of the patient, an area for comments, and the procedure to be accomplished. Note that this list is not complete nor is it closed, and any reasonable set of categories will suffice.

The calendar automatically updates to incorporate a new appointment. If one of the fields is entered incorrectly—for example, the area code is missing in the phone number—then an error message occurs alerting the user that the appointment has not been incorporated. In one embodiment, an appointment will still be incorporated even if errors are present in one or more fields.

In one embodiment, the scheduler identifies and displays the total number of appointments for a given day. In another embodiment, the scheduler identifies and displays the number of appointments that have been completed for that day. In yet another embodiment, the scheduler identifies and displays the number of appointments left for a given day.

In one embodiment, the Office Management Tool comprises a Patient Search for searching through a database of patients. This Patient Search may be accessed from a link to a separate page, a drop down menu, a spoke on a hub and spoke, or an expandable/collapsible pane, panel, or cell. The search query features may limit the search, at the command of the user, to patients of one gender, patients who have appointments on a given day, patients undergoing a particular procedure, patients whose appointments are scheduled at a particular office, as well as other categories. The user may search by first name, last name, social security number, gender, phone number, or date of birth. The results of the search query are displayed in the user interface. When a search is completed, the user may order the search results according to one or more of these categories, i.e., ordering the list by last name in alphabetical or reverse alphabetical order. In another embodiment, the user interface displays a list of all patients whose first or last name begins with a letter selected by the user.

In one embodiment, the Office Management Tool comprises an Add Patient means. This means may include a link to a separate page, a drop down menu, a spoke on a hub and spoke, or an expandable/collapsible pane, panel, or cell. The Add Patient means comprises one or more drop-down menus, fields, radio buttons, toggle buttons, or other user interface interactive means. A non-exclusive list items include a first name, last name, social security number, date of birth, gender, email, and phone number.

In one embodiment, the user can create an appointment for the patient on the same page that he or she adds the patient to the system. This Add Appointment feature is already described above.

In one embodiment, the Office Management Tool comprises an Inbox. This inbox may appear as its own link to a separate page, a drop down menu, a spoke on a hub and spoke, or an expandable/collapsible pane, panel, or cell. The Inbox comprises a table of patient names. Associated with each name are visit dates, reports, images, requisition numbers, status, reception dates, sign of, remarks, and a file upload.

The Patient Management Tool comprises one or more Accordion menus. An Accordion menu is a vertically stacked list of sub-menus. The sub-menus remain collapsed, so that only the name of the sub-menu is visible, until selected. Upon selection, the sub-menu opens or expands, so that the user can access the functionality within. While generally Accordion menus permit several sub-menus to remain open at once, the Office Management Tool described herein may also comprise One-Note Accordion menus. A One-Note Accordion menu permits only one sub-menu to remain open at a given time. When a second sub-menu is selected, the first sub-menu closes.

In one embodiment, the Patient Management Tool comprises an Image Organization Means. In one embodiment, the Image Organization Means comprises an accordion menu. In this embodiment, each sub-menu is labeled with a given date, and its contents include thumbnails of images taken on or assigned that given date. In one embodiment, one or more images can be opened by selecting their thumbnails, and these images can be compared displayed simultaneously in order to compare them. In one embodiment, each Report, to be described below, has its own accordion menu that displays images uploaded or otherwise entered into the report. In another embodiment, an image-based accordion menu may be assigned to each patient account. In this way, the accordion shows a chronological picture history of the patient.

In one embodiment, the Patient Management Tool comprises a Health Insurance Claim Form. In one embodiment, the Health Insurance Claim Form comprises an accordion menu. In this embodiment, each sub-menu is labeled with a different field, including Insurance Name, Insured's IC Number, Patient's Name, Patient's birth date, Insured's Name, Insured's Policy or Group Number, Insured's Date of Birth, Insured's Employer's name or school name, Insured's insurance place name or program name, Patient's Address, Patient's relationship to Insured, Insured's address, Patient Status, as well as any other facts or figures relevant to the an insurance claim form.

In one embodiment, the Patient Management Tool comprises a Reports section. The Reports section comprises a template panel, in which a template is displayed. The template comprises a set of categories and fields in which a user can enter or select one or more words, terms, or sentences.

In one embodiment, the Reports section comprises a template drop down menu from which a template can be selected. That template is then displayed in the template panel. In another embodiment, the Reports section further comprises an image panel, in which one or more images relating to a given report are displayed. In one embodiment, these images can be expanded so that they can be seen in greater detail, either individually, or as a group, or they can be selected to open up in another page.

In one embodiment, the Reports section comprises a details panel. When one of the categories in the template panel is selected, a list of terms and/or categories of terms are displayed in the details panel. If a category is selected, one or more terms are displayed in a drop-down menu or as an accordion menu. One or more of these terms can be selected to populate the template panel fields. In one embodiment, the fields are formatted to receive codes, wherein the codes represent terms or words. For example a diagnosis field may only accept diagnosis codes.

In one embodiment, the diagnosis codes, frequently referred to as CPT (current procedural terminology) codes, are matched to advertisements in a process known as Initiated Narrowcasting Advertising. CPT codes that are frequently entered by a given user may be automatically matched to advertisements embedded in the program, which are then displayed somewhere in the program's user interface, or those codes are uploaded via a network connection to one or more databases and/or processing locations. Advertisements, which are tagged automatically or manually to those code, are then downloaded by the one or more computers hosting the program; these advertisements are then displayed somewhere on the program's user interface.

In one embodiment, the Reports section features a signature block. This signature block can be displayed separately from the other components of the Reports section, or as part of another component. For example, it can appear as a field within the template panel.

In one embodiment, the Reports section comprises an export button. When selected, the information entered into the Reports section is transformed into a document such as a PDF. This document can then be saved to the user's computer, emailed, or stored elsewhere in the Patient Management Tool.

In one embodiment, the Reports section may suggest a term or tag to the user; if this term or tag is verified, either through a selection or by lack of a rejection substantiated by a selection, then that term or tag attaches to the report. One or more terms or tags may be searched in a report database by the user, thereby causing the display of the one or more reports that have those one or more terms or tags attached to them.

In one embodiment, the fields available in the template panel change as information is entered into the template panel. In one embodiment, the page may reload so that new fields become displayed. In another embodiment, fields may remain visible, but information cannot be entered into them. In one embodiment, fields and/or field terms become available/unavailable due to the diagnosis entered. In this embodiment, only procedures that are indicated as approved for a given diagnosis by a database internal or external to the Patient Management Tool may be entered in a procedure field.

In one embodiment, the Patient Management Tool may receive visual data from an optical instrument that records images and can transmit them to another location. This visual data may comprise static images, such as photographs, or dynamic images, such as video. The Patient Management Tool may comprise a display window, which may be a part of another page or its own separate page. The display window displays the visual data, which is either received and displayed in real time, or is stored on a computer readable medium such as the RAM, a CD, or a hard disc.

In one embodiment, the visual data may be modified or annotated within the display window of the Patient Management tool or in a separate image editor. The user may interact with the visual data by clicking or selecting an area on the visual data, whether it is a static image or a video. If the visual data being clicked or selected is a video, then the click or selection will receive a time stamp for the time interval and duration for which the area on the visual data is selected. This click or selection will be visible when the image or video is displayed and/or played.

In another embodiment, the user may leave a comment directed to the click or selection. This comment may comprise text, shapes, drawings, and/or colors. In one embodiment, the comment may be displayed alongside the clicked or selected area. In another embodiment, a line will be drawn between the clicked or selected area and an area in which the comment is displayed.

In one embodiment, the visual data, with or without click or selection points and/or comments are accessible in real time over a network, enabling another user to view, click, select, and/or comment on various areas. The visual data may be captured by the optical device, transmitted to a local computer, saved in a computer data storage medium, uploaded via a network to one or more servers, and downloaded to one or more other data storage mediums. In one embodiment, the image can only be uploaded to a virtual private network.

The optical instrument that provides the visual data may be an endoscope, as described elsewhere in this application.

In one embodiment, the Patient Management tool displays the image captured by the endoscope in real time. In another embodiment, the endoscope has a capture button; when pressed or otherwise selected by the user, the endoscope captures an image through the use of its image-capturing means, such as a camera. This analog image is recorded digitally onto a computer readable storage device, such as RAM, a hard drive, or a disc, and then may be displayed by the Patient Management Tool. In one embodiment, the Patient Management Tool uploads the image to a server or another computer via a network. In another embodiment, the endoscope has a freeze button; when pressed or otherwise selected by the user, the image displayed in the display window is not replaced by any other image, but is instead held statically, until the freeze button is unpressed or unselected by the user. In this sense, it is "frozen" in place until "unfrozen". In one embodiment, if the freeze button is held for a predetermined duration, then the frozen image is automatically saved permanently to a computer readable storage device, preferably a hard drive. If the freeze button is held less than a predetermined duration, then the frozen image is saved only temporarily in the RAM; once the image is unfrozen, it is deleted from the RAM.

In one embodiment, one or more users who are accessing the same visual data or data set may also communicate in a text message box in the same or a separate page from that in which the visual data is displayed. In another embodiment, one or more users may also communicate through a microphone and speaker system; one or more computers may have a microphone and/or a speaker through which they may give and/or receive vocal communications.

Typically, images are captured in a raw format, converted into a digital format, saved temporarily in the browser's cache until they are uploaded via the internet to one or more servers, and then deleted. Before the images are uploaded, they are at risk of being erased if the browser crashes.

Here, the images are saved locally but in a permanent manner, such as to a hard disk, and then deleted once they are uploaded. This protects the images from intervening errors or mishaps.

An endoscope is a medical device used in an endoscopy, the interior examination of an organ or body cavity. Unlike topical examinations, in which there is a barrier such as the epidermis that prevents both sight and substantially touch, an endoscopy involves the insertion of the endoscope into the organ or body cavity, thereby permitting sight into a location that is otherwise hidden and dark. Unlike other medical imaging devices, such as X-Ray CT, there are no adverse risks resulting from radiation or other exposures.

The endoscope may comprise a lighting system to illuminate the area, an image transmitting system for creating an image of the area and transmitting the image to the user in a way that the user can see the image, and a tube or cable through which the image is transmitted. In addition, one or more medical instruments may be attached to the endoscope for purposes such as capturing a sample, applying treatment, or removing unwanted growths.

There are many areas in which an endoscope can be employed; the name, structure, and components of the endoscope differ by these areas. For example, when the endoscope is used to explore the rectum or anus, it is referred to as a proctoscope and comprises a short tube. When the endoscope is used to explore the lower respiratory tract, it is referred to as a bronchoscope and comprises a long, thin tube. Generally, endoscopes are entered into body cavities or organs through naturally occurring orifices, but there are some endoscopes, known as Laparoscopes, designed to be inserted through surgically created orifices. In addition to the numerous medical applications, endoscopes or devices substantially similar to endoscopes are frequently utilized in such areas as criminal surveillance, technical systems, and film as art. For the purposes of this application, "endoscope" refers to any device that captures visual data, whether static or dynamic, and transforms it into digital data, whether in the medical field or any other field.

The invention claimed is:

1. A system including an endoscope, a light source, and a first computer system, the light source coupled to the endoscope, the endoscope configured to transmit visual data to the first computer system, the first computer system comprising a processor, computer storage memory, a first set of one or more input devices, and a first display device, the first computer system connected to a network of one or more computer systems, each computer system being operated by a user, the each computer system comprising a unique identification code;

the processor programmed to:
  receive a launch procedure instruction from a first user using the first set of one or more input devices, then begin tracking a time during which a first procedure is active and display a procedure window on the first display device; receive visual data from the endoscope, then convert the visual data into display data, and then display the display data in the procedure window on the first display device; and
  receive a capture instruction from the first user using the endoscope, then save one or more frames of the display data as a captured media object;
  receive a view request from a second user using a second set of input devices, then display the procedure window on a second display device, the second display device connected to a second computer system operated by the second user, the second computer system connected to the first computer system through the network of computer systems;
  associate one or more name elements with a first set of one or more time elements, associate one or more empty elements with a second set of one or more time elements, graphically display the one or more time elements in a first axis on the first display device, and graphically display the one or more name elements and the one or more empty elements in a second axis perpendicular to the first axis on the first display device;
  receive a user selection of a first name element from the first user using the first set of one or more input devices and then display patient information associated with the first name element on the first display device;
  receive a user selection of a first empty element associated with a first time element from the first user using the first set of one or more input devices and then display a patient search field on the first display device, receive a user text entry in the patient search field from the first user, then search a patient database using the user text entry, and then display one or more resultant name elements;

receive a user selection of a first resultant name element from the first user using the first set of one or more input devices, then cease associating the first empty element with the first time element, cease displaying the first empty element, associate the first resultant name element with the first time element, and display the first resultant name element in a graphical position previously occupied by the first empty element;

receive an annotation instruction from the first user using the first set of one or more input devices, then display an annotation window on the first display device and display thumbnails of captured media objects; receive a user selection of a first thumbnail, then display a first media object in the annotation window; receive a user selection of a first graphical position on the first media object from the first user using the first set of one or more input devices, then display a first annotation field adjacent to the first graphical position; receive a first annotation entry in the first annotation field, then embed the first annotation entry and the first graphical position in the first media object and attach metadata from the first user to the first media object;

receive an annotate request from the second user using the second set of input devices, then display the annotation window on the second display device; receive a user selection of a second graphical position on the first media object from the second user using the second set of one or more input devices, then display a second annotation field adjacent to the second graphical position; receive a second annotation entry in the second annotation field, then embed the second annotation entry, embed the second graphical position in the first media object, and attach metadata from the second user to the first media object, then display the second annotation entry adjacent to a third graphical position corresponding to the second graphical position on the first display device;

display a report window and a list of templates in the report window on the first display device, then receive a user selection of a first template from the first user using the first set of one or more input devices, then display the first template in a first template window on the first display device and display one or more template fields on the first template, then receive a user selection of a first template field, then display a tree of terms in a second template window of the second template on the first display device, then receive a user selection of a first term from the tree of terms, then display the first term in the first template field;

receive a user selection of a second thumbnail from the first user using the first set of one or more input devices, then display a second media object in the annotation window of the first display device, then receive a user selection of a fourth graphical position on a second media object, then display a third annotation field adjacent to the fourth graphical position, then receive a third annotation entry in the third annotation field, then receive a user selection of a fifth graphical position on the second media object, then display a fourth annotation field adjacent to the fifth graphical position, then receive a fourth annotation entry in the fourth annotation field, then embed the third annotation entry, the fourth annotation entry, the fourth graphical position, and the fifth graphical position in the second media object, then if a user selection of a second template is received from the first user, determine if the third annotation entry is textually equivalent to a first category listed on the second template, and if the third annotation entry is textually equivalent to the first category, then display the fourth annotation entry in a field adjacent to the first category on the first display device;

display a lock report button, then receive a user selection of the lock report button for a first report, then if a first set of changes are received from the first user after the lock report button has been selected, save a first record of the first set of changes, a first time, and a first date when the first set of changes are made, and a first username for the first user in a first record, and then associate the first record with the first report;

if a second set of changes are received from the second user after the lock report button has been selected, save a second record of the second set of changes, a second time, and a second date when the second set of changes are made, and a second username for the first user in a second record, and associate the second record with the first report; and display an export button, then receive a user selection of the export button from the first user using the first set of one or more input devices, then encrypt an export file, then transmit the export file to a predetermined destination in a predetermined format.

2. The system in claim 1, the processor further programmed to: receive a user selection of a diagnosis field of the second template from the first user using the first set of one or more input devices, then display a first diagnosis window and a second diagnosis window on the first display device, then display a list of codes in the second diagnosis window and display a diagnosis search field in the first diagnosis window, then receive a user selection of a first code from the first diagnosis window, then display the first code in the second diagnosis window;

receive a user selection of a second code in the second diagnosis window from the first user using the first set of one or more input devices, then display the second code in the diagnosis field of the first template; and if a second term is entered into a second template field, determine whether the second term is associated with the second code, and if the second term is not associated with the second code, display a warning; identify an advertisement associated with the second code, display the advertisement.

3. The system in claim 2, where the one or more codes are CPT codes.

4. The system in claim 2, where the one or more codes are ICD codes.

5. The system in claim 2, where the scope is an endoscope.

6. The system in claim 2, where the scope is a laproscope.

7. The system in claim 2, where the scope is an arthroscope.

8. The system in claim 2, where the scope is a vascularscope.

9. The system in claim 2, where the scope is a gynecological scope.

10. A system including an scope, a light source, and a computer system, the light source coupled to the scope, the scope configured to transmit visual data to the computer system, the computer system comprising a processor, computer storage memory, one or more input devices, and a display device;

the processor programmed to:

receive a launch procedure instruction from a user using the one or more input devices, then begin tracking a time during which a first procedure is active and display a procedure window on the display device; receive visual data from the scope, then convert the visual data into display data, and then display the display data in the procedure window on the display device; receive a capture instruction from the user using the scope, then save one or more frames of the display data as a captured media object;

associate one or more name elements with a first set of one or more time elements, associate one or more empty elements with a second set of the one or more time elements, graphically display the one or more time elements in a first axis on the display device, and graphically display the one or more name elements and the one or more empty elements in a second axis perpendicular to the first axis on the display device;

receive a user selection of a first name element from the user using the one or more input devices and then display patient information associated with the first name element on the display device;

receive a user selection of a first empty element associated with a first time element from the user using the one or more input devices and then display a patient search field on the display device, receive a user text entry in the patient search field, then search a patient database using the user text entry, and then display one or more resultant name elements; and receive a user selection of a first resultant name element from the user using the one or more input devices, then cease associating the first empty element with the first time element, cease displaying the first empty element, associate the first resultant name element with the first time element, and display the first resultant name element in a graphical position previously occupied by the first empty element.

11. The system in claim 10, the processor additionally programmed to: receive an annotation instruction from the user using the one or more input devices, then display an annotation window on the display device and display thumbnails of captured media objects; receive a user selection of a first thumbnail, then display a first media object in the annotation window; receive a user selection of a first graphical position on the first media object from the user using the one or more input devices, then display a first annotation field adjacent to the first graphical position; receive a first annotation entry in the first annotation field, then embed the first annotation entry and the first graphical position in the first media object and attach metadata from the user to the first media object.

12. The system in claim 10, the processor additionally programmed to: display a report window and a list of templates in the report window on the display device, then receive a user selection of a first template from the user using the one or more input devices, then display the first template in a first template window on the display device and display one or more template fields on the first template, then receive a user selection of a first template field, then display a tree of terms in a second template window on the display device, then receive a user selection of a first term from the tree of terms, then display the first term in the first template field.

13. The system in claim 11, the processor additionally programmed to: receive a user selection of a second thumbnail from the user using the one or more input devices, then display a second media object in the annotation window of the display device, then receive a user selection of a second graphical position on a second media object, then display a second annotation field adjacent to the second graphical position, then receive a second annotation entry in the second annotation field, then receive a user selection of a third graphical position on the second media object, then display a third annotation field adjacent to the third graphical position, then receive a third annotation entry in the third annotation field, then embed the second annotation entry, the third annotation entry, the second graphical position, and the third graphical position in the second media object, then if a user selection of a second template is received from the user, determine if the second annotation entry is textually equivalent to a first category listed on the second template, and if the second annotation entry is textually equivalent to the first category, then display the third annotation entry in a field adjacent to the first category on the display device.

14. The system in claim 13, the processor additionally programmed to: receive a user selection of a diagnosis field from the user using the one or more input devices, then display a first diagnosis window and a second diagnosis window on the display device, then display a list of CPT codes in the second diagnosis window and display a diagnosis search field in the first diagnosis window, then receive a user selection of a first CPT code from the first diagnosis window, then display the first CPT code in the second diagnosis window; receive a user selection of a second CPT code in the second diagnosis window from the user using the one or more input devices, then display the second CPT code in the diagnosis field.

15. The system in claim 14, the processor additionally programmed to: if a second term is entered into a second template field, determine whether the second term is associated with the second CPT code, and if the second term is not associated with the second CPT code, display a warning; identify an advertisement associated with the second CPT code and display the advertisement.

16. The system in claim 10, the processor additionally programmed to: display a lock report button, receive a user selection of the lock report button for a report, then if a set of changes are received from the user after the lock report button has been selected, save a record of the set of changes, a time, and a date when the set of changes are made, and a username for the user in a record, and associate the record with the report.

17. The system in claim 10, the processor additionally programmed to: display an export button, then receive a user selection of the export button from the user using the one or more input devices, then encrypt an export file, then transmit the export file to a predetermined destination in a predetermined format.

18. A system including an scope, a light source, and a first computer system, the light source coupled to the scope, the scope configured to transmit visual data to the first computer system, the first computer system comprising a processor, computer storage memory, a first set of one or more input devices, and a first display device, the first computer system connected to a network of one or more computer systems, each computer system being operated by a user, the each computer system comprising a unique identification code;

the processor programmed to:

receive a launch procedure instruction from a first user using the first set of one or more input devices, then begin tracking a time during which a first procedure is active and display a procedure window on the first display device; receive visual data from the scope, then convert the visual data into display data, and then display the display data in the procedure window on the first display device; receive a capture instruction from the first user using the scope and then save one or more frames of the display data as a captured media object; and receive an annotation instruction from the first user using the first set of one or more input devices, then display an annotation window on the first display device and display thumbnails of captured media objects; receive a user selection of a first thumbnail, then display a first media object in the annotation window; receive a user selection of a first graphical position on the first media object from the first user using the first set of one or more input devices, then display a first annotation field adjacent to the first graphical position; receive a first annotation entry in the first annotation field, then embed the first annotation entry and the first graphical position in the first media object and attach metadata from the first user to the first media object.

19. The system in claim 18, the processor programmed to: display a report window and a list of templates in the report window on the first display device, then receive a user selection of a first template from the first user using the first set of one or more input devices, then display the first template in a first template window on the first display device and display one or more template fields on the first template, then receive a user selection of a first template field, then display a tree of terms in a second template window on the first display device, then receive a user selection of a first term from the tree of terms, then display the first term in the first template field.

20. The system in claim 19, the processor programmed to: receive a user selection of a second thumbnail from the first user using the first set of one or more input devices, then display a second media object in the annotation window of the first display device, then receive a user selection of a second graphical position on a second media object, then display a second annotation field adjacent to the second graphical position, then receive a second annotation entry in the second annotation field, then receive a user selection of a third graphical position on the second media object, then display a third annotation field adjacent to the third graphical position, then receive a third annotation entry in the third annotation field, then embed the second annotation entry, the third annotation entry, the second graphical position, and the third graphical position in the second media object, then if a user selection of a second template is received from the first user, determine if the second annotation entry is textually equivalent to a category listed on the second template, and if the second annotation entry is textually equivalent to the category, then display the third annotation entry in a field adjacent to the category on the first display device.

21. The system in claim 18, the processor programmed to: receive a user selection of a diagnosis field of a second template from the first user using the first set of one or more input devices, then display a first diagnosis window and a second diagnosis window on the first display device, then display a list of CPT codes in the second diagnosis window and display a diagnosis search field in the first diagnosis window, then receive a user selection of a first CPT code from the first diagnosis window, then display the first CPT code in the second diagnosis window; receive a user selection of a second CPT code in the second diagnosis window from the first user using the first set of one or more input devices and then display the second CPT code in the diagnosis field of the first template.

22. The system in claim 21, the processor programmed to: if a second term is entered into a second template field, determine whether the second term is associated with the second CPT code, and if the second term is not associated with the second CPT code, display a warning; identify an advertisement associated with the second CPT code, and display the advertisement.

23. The system in claim 19, the processor programmed to: display a lock report button, then receive a user selection of the lock report button for a first report, then if a first set of changes are received from the first user after the lock report button has been selected, save a first record of the first set of changes, a first time, and a first date when the first set of changes are made, and a first username for the first user in a first record, and then associate the first record with the first report.

24. The system in claim 23, the processor programmed to: if a second set of changes are received from a second user after the lock report button has been selected, save a second record of the second set of changes, a second time, and a second date when the second set of changes are made, and a second username for the first user in a second record, and then associate the second record with the first report.

25. The system in claim 19, the processor programmed to: receive a view request from a second user using a second set of input devices, then display the procedure window on a second display device, the second display device connected to a second computer system operated by the second user, the second computer system connected to the first computer system through the network of computer systems.

26. The system in claim 25, the processor programmed to: receive an annotate request from the second user using the second set of input devices, then display the annotation window on the second display device; receive a user selection of a second graphical position on the first media object from the second user using the second set of one or more input devices, then display a second annotation field adjacent to the second graphical position; receive a second annotation entry in the second annotation field, then embed the second annotation entry, embed the second graphical position in the first media object, and attach metadata from the second user to the first media object, then display the second annotation entry adjacent to a third graphical position corresponding to the second graphical position on the first display device.

27. The system in claim 19, the processor programmed to: display an export button, then receive a user selection of the export button from the first user using the first set of one or more input devices, then encrypt an export file, then transmit the export file to a predetermined destination in a predetermined format.

28. The system in claim 19, the processor programmed to: display a set of privacy options, then receive a user selection of a first privacy option, then remove patient identification information from an export file.

29. The system in claim 19, the processor programmed to: associate one or more name elements with a first set of one or more time elements, associate one or more empty elements with a second set of one or more time elements, graphically display the one or more time elements in a first axis on the first display device, and graphically display the one or more name elements and the one or more empty elements in a second axis perpendicular to the first axis on the first display device;

receive a user selection of a first name element from the first user using the first set of one or more input devices and then display patient information associated with the first name element on the first display device;

receive a user selection of a first empty element associated with a first time element from the first user using the first set of one or more input devices and then display a patient search field on the first display device, receive a user text entry in the patient search field from the first user, then search a patient database using the user text entry, and then display one or more resultant name elements; and receive a user selection of a first resultant name element from the first user using the first set of one or more input devices, then cease associating the first empty element with the first time element, cease displaying the first empty element, associate the first resultant name element with the first time element, and display the first resultant name element in a graphical position previously occupied by the first empty element.

30. The system in claim 18, where the scope is an endoscope.

31. The system in claim 18, where the scope is a laproscope.

32. The system in claim 18, where the scope is an arthroscope.

33. The system in claim 18, where the scope is a vascularscope.

34. The system in claim 18, where the scope is a gynecological scope.

\* \* \* \* \*